(12) United States Patent
Niazi

(10) Patent No.: US 11,497,899 B2
(45) Date of Patent: Nov. 15, 2022

(54) INTRA-ESOPHAGEAL BALLOON SYSTEM

(71) Applicant: Niazi Licensing Corporation, Olympia, WA (US)

(72) Inventor: Imran K. Niazi, Milwaukee, WI (US)

(73) Assignee: Niazi Patent Holdings, LLC, River Hills, WI (US)

( * ) Notice: Subject to any disclaimer, the term of this patent is extended or adjusted under 35 U.S.C. 154(b) by 849 days.

(21) Appl. No.: 16/007,461

(22) Filed: Jun. 13, 2018

(65) Prior Publication Data

US 2018/0289934 A1 Oct. 11, 2018

Related U.S. Application Data

(60) Continuation-in-part of application No. 15/786,707, filed on Oct. 18, 2017, which is a division of
(Continued)

(51) Int. Cl.
*A61M 25/10* (2013.01)
*A61M 29/02* (2006.01)
(Continued)

(52) U.S. Cl.
CPC ......... *A61M 25/1002* (2013.01); *A61B 18/00* (2013.01); *A61B 18/02* (2013.01); *A61B 18/1492* (2013.01); *A61B 34/70* (2016.02); *A61B 34/71* (2016.02); *A61B 34/73* (2016.02); *A61M 25/10181* (2013.11); *A61M 29/02* (2013.01); *A61B 90/04* (2016.02);
(Continued)

(58) Field of Classification Search
CPC .............. A61M 25/1002; A61M 29/02; A61M 25/10181; A61M 2025/1059; A61M 2025/1047; A61M 25/10185
See application file for complete search history.

(56) References Cited

U.S. PATENT DOCUMENTS 2,077,453 A 3/1934 Albright
4,576,142 A * 3/1986 Schiff ................. A61M 25/104
604/914
(Continued)

FOREIGN PATENT DOCUMENTS

WO 2018065047 4/2018
WO 2019174708 9/2019

*Primary Examiner* — Thomas McEvoy
(74) *Attorney, Agent, or Firm* — Boyle Fredrickson S.C.

(57) ABSTRACT

A balloon is provided for selectively moving an esophagus away from an ablation site. The balloon is received through an oral cavity and into the esophagus of a patient. A deflecting member is provided in the tube, the balloon, or both, so as to selectively distort to bend the balloon and/or the tube to move the esophagus away from the ablation site. The deflecting member may comprise at least one of a strip made of a shape memory material that is responsive to the receipt of a stimulus to deflect to a predetermined shape, a strip that is made of or contains a ferrous material and that deflects in response to the presence of a magnetic field, and a selectively tensionable cable, wire, or string. The deflecting member may be supplemented by a stiffening strip that is located in the balloon and that causes the balloon to expand circumferentially and asymmetrically when inflated.

17 Claims, 24 Drawing Sheets

Related U.S. Application Data application No. 12/847,018, filed on Jul. 30, 2010, now Pat. No. 9,937,329.

(60) Provisional application No. 61/272,564, filed on Oct. 6, 2009.

(51) Int. Cl.

| | |
|---|---|
| *A61B 18/00* | (2006.01) |
| *A61B 18/02* | (2006.01) |
| *A61B 18/14* | (2006.01) |
| *A61B 34/00* | (2016.01) |
| *A61B 17/00* | (2006.01) |
| *A61B 17/22* | (2006.01) |
| *A61B 90/00* | (2016.01) |

(52) U.S. Cl.
CPC ........... *A61B 2017/00243* (2013.01); *A61B 2017/00323* (2013.01); *A61B 2017/00557* (2013.01); *A61B 2017/00867* (2013.01); *A61B 2017/22051* (2013.01); *A61B 2018/00011* (2013.01); *A61B 2018/0022* (2013.01); *A61B 2018/00023* (2013.01); *A61B 2018/00345* (2013.01); *A61B 2018/00351* (2013.01); *A61B 2018/00488* (2013.01); *A61B 2018/00577* (2013.01); *A61B 2018/0212* (2013.01); *A61B 2018/0262* (2013.01); *A61B 2090/0427* (2016.02); *A61M 25/10185* (2013.11); *A61M 2025/1047* (2013.01); *A61M 2025/1059* (2013.01); *A61M 2025/1084* (2013.01); *A61M 2205/0266* (2013.01)

(56) References Cited

U.S. PATENT DOCUMENTS

| | | | | |
|---|---|---|---|---|
| 4,955,377 | A | 9/1990 | Lennox et al. | 837/105 |
| 5,048,532 | A | 9/1991 | Hickey | 600/488 |
| 5,531,776 | A | 7/1996 | Ward et al. | 607/105 |
| 5,662,608 | A | 9/1997 | Imran | A61M 25/1002 |
| | | | | 604/103.07 |
| 5,716,386 | A | 2/1998 | Ward et al. | 607/106 |
| 5,766,151 | A | 6/1998 | Valley et al. | 604/103.07 |
| 6,015,382 | A | 1/2000 | Zwart | A61B 17/0218 |
| | | | | 600/207 |
| 6,146,339 | A | 11/2000 | Biagtan | A61B 25/09 |
| | | | | 600/585 |
| 6,217,548 | B1 | 4/2001 | Tsugita et al. | |
| 7,101,387 | B2 | 9/2006 | Garabedian et al. | |
| 7,621,908 | B2 | 11/2009 | Miller | |
| 8,506,589 | B2 | 8/2013 | Maloney | |
| D806,231 | S | 12/2017 | Fojtik | |
| D806,860 | S | 1/2018 | Fojtik | |
| 9,931,108 | B2 | 4/2018 | Miller | |
| 10,307,520 | B2 | 6/2019 | Oza et al. | |
| 10,335,133 | B2 | 7/2019 | Fojtik | |
| 10,478,263 | B2 | 11/2019 | Allmendinger et al. | |
| 10,695,041 | B2 | 6/2020 | Fojtik | |
| 2003/0144682 | A1 | 7/2003 | Qureshi et al. | |
| 2004/0020491 | A1 | 2/2004 | Fortuna | |
| 2004/0116851 | A1* | 6/2004 | Johansen | A61M 25/0155 |
| | | | | 604/103.04 |
| 2004/0210281 | A1 | 10/2004 | Dzeng et al. | |
| 2006/0118127 | A1 | 6/2006 | Chinn | |
| 2007/0055328 | A1 | 3/2007 | Mayse et al. | |
| 2007/0066968 | A1 | 3/2007 | Rahn | |
| 2007/0118097 | A1 | 5/2007 | Miller | |
| 2008/0033415 | A1 | 2/2008 | Rleker et al. | |
| 2008/0125708 | A1 | 5/2008 | Feng | |
| 2008/0161890 | A1* | 7/2008 | Lafontaine | A61B 18/1492 |
| | | | | 607/105 |
| 2008/0177175 | A1 | 7/2008 | Mottola et al. | 600/424 |
| 2008/0243112 | A1 | 10/2008 | De Neve | |
| 2009/0069875 | A1 | 3/2009 | Fishel | |
| 2019/0223734 | A1 | 7/2019 | Lakkireddy et al. | |
| 2019/0269834 | A1 | 9/2019 | Oza et al. | |
| 2020/0029822 | A1 | 1/2020 | Morris et al. | |

\* cited by examiner

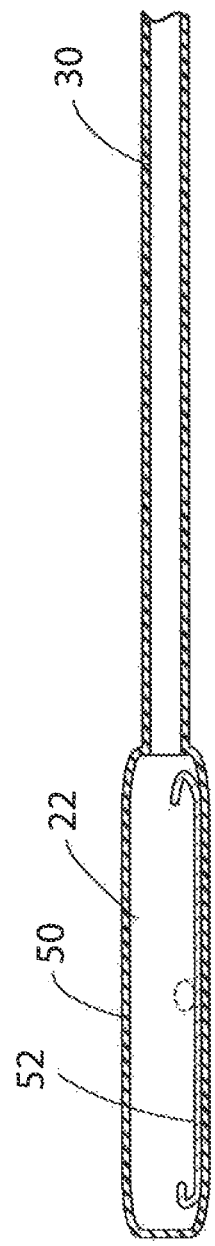
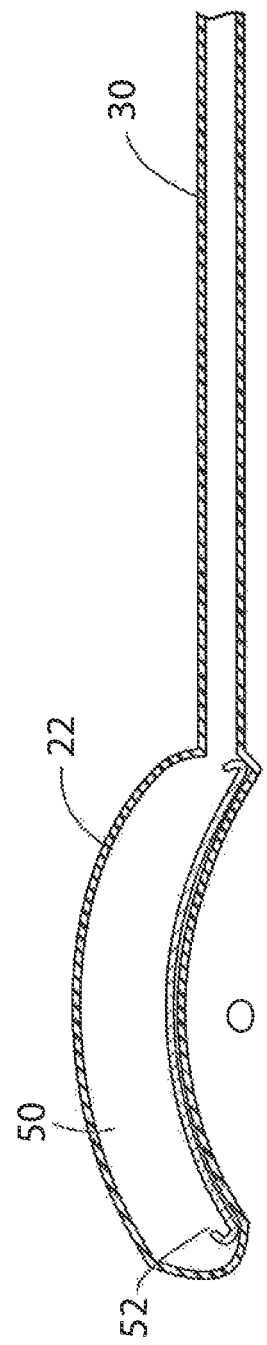

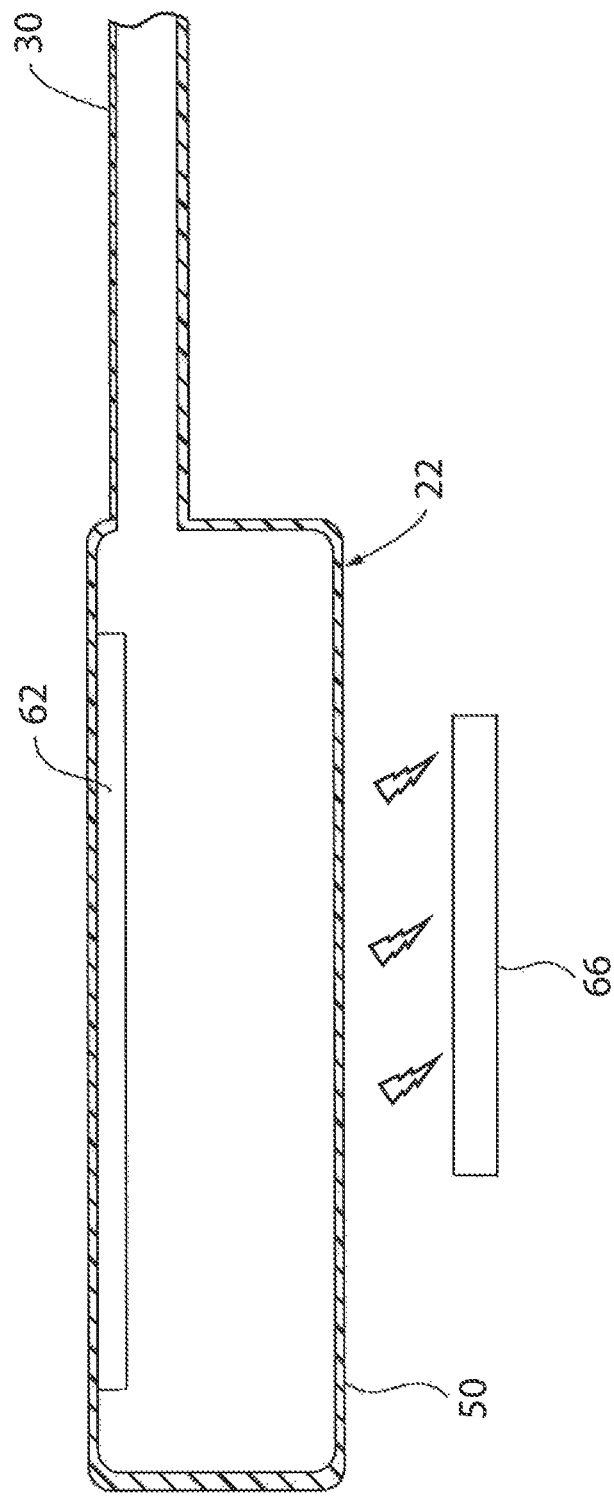

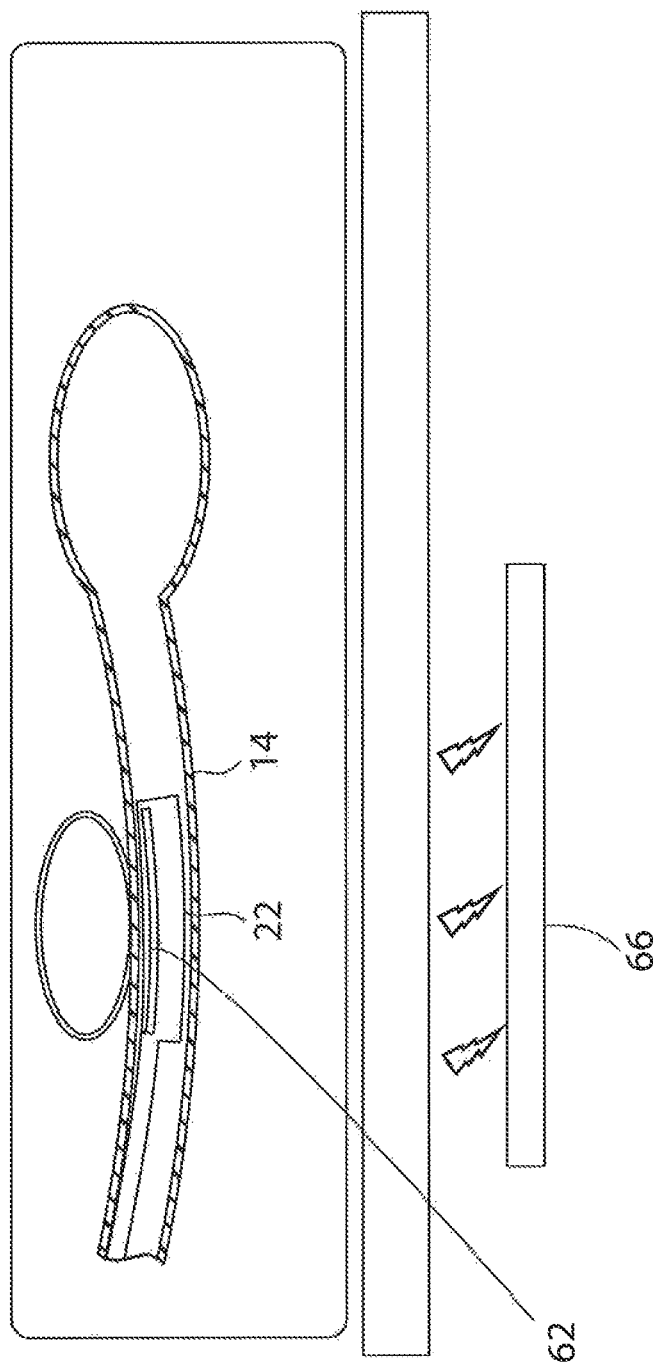

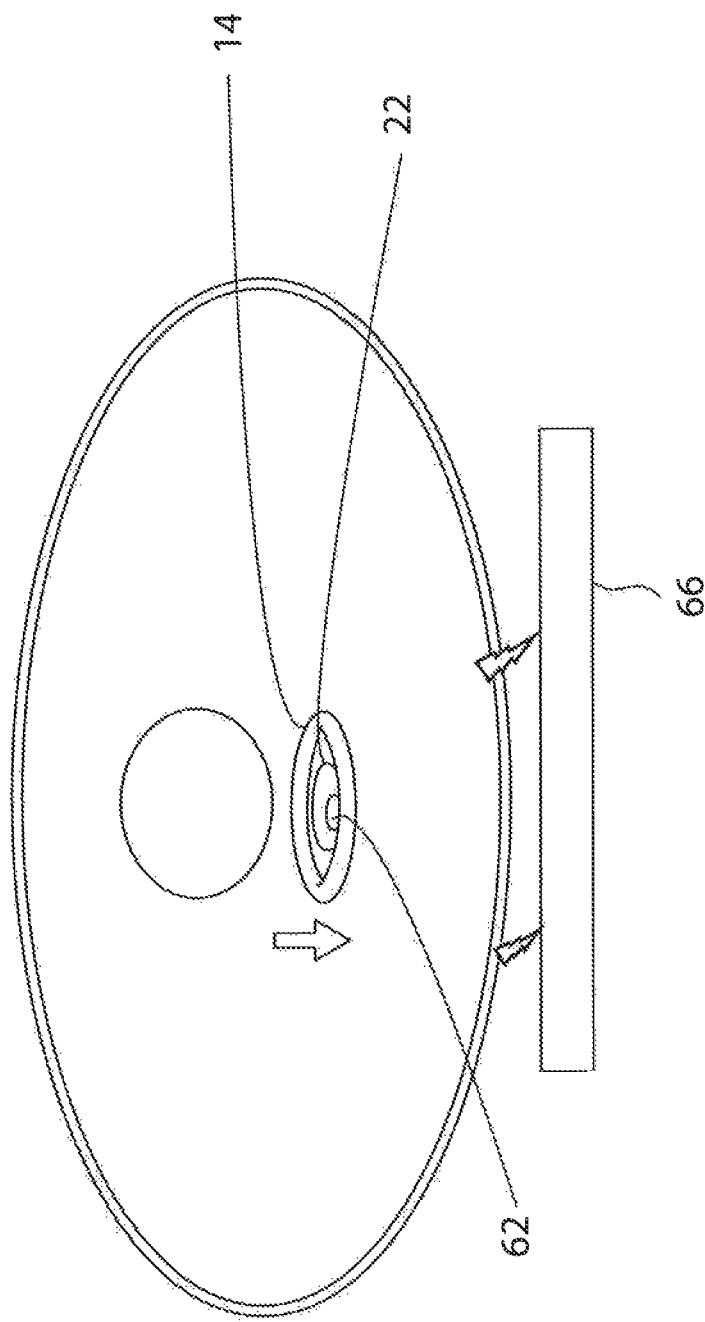

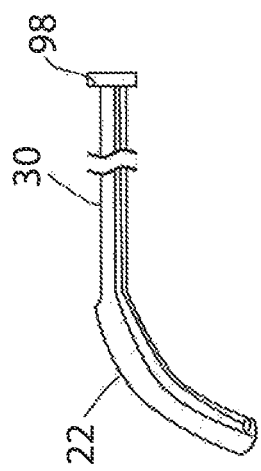
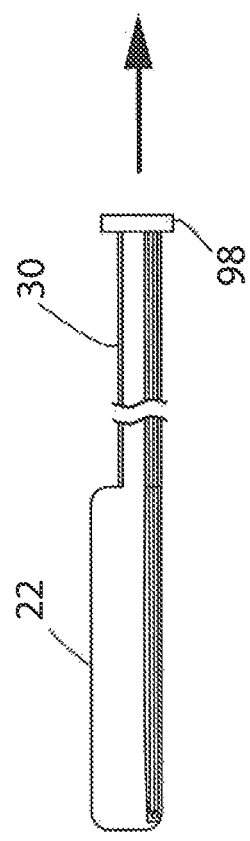
FIG. 6C

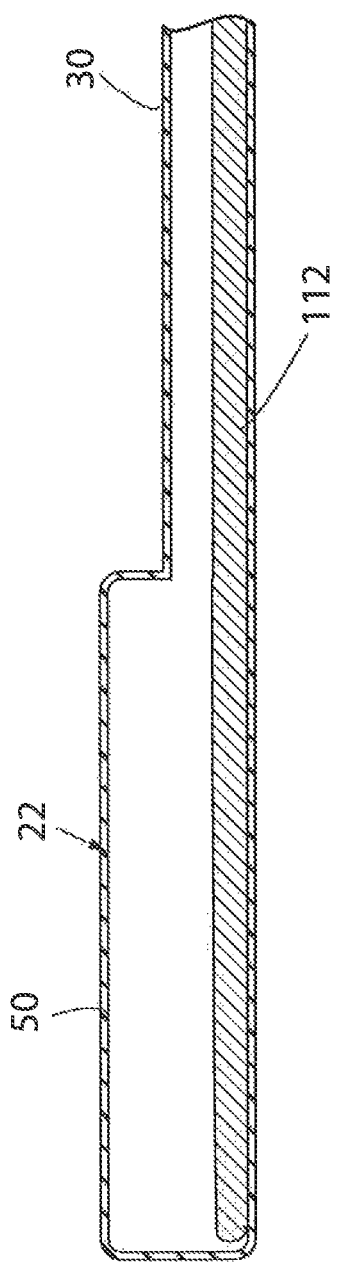

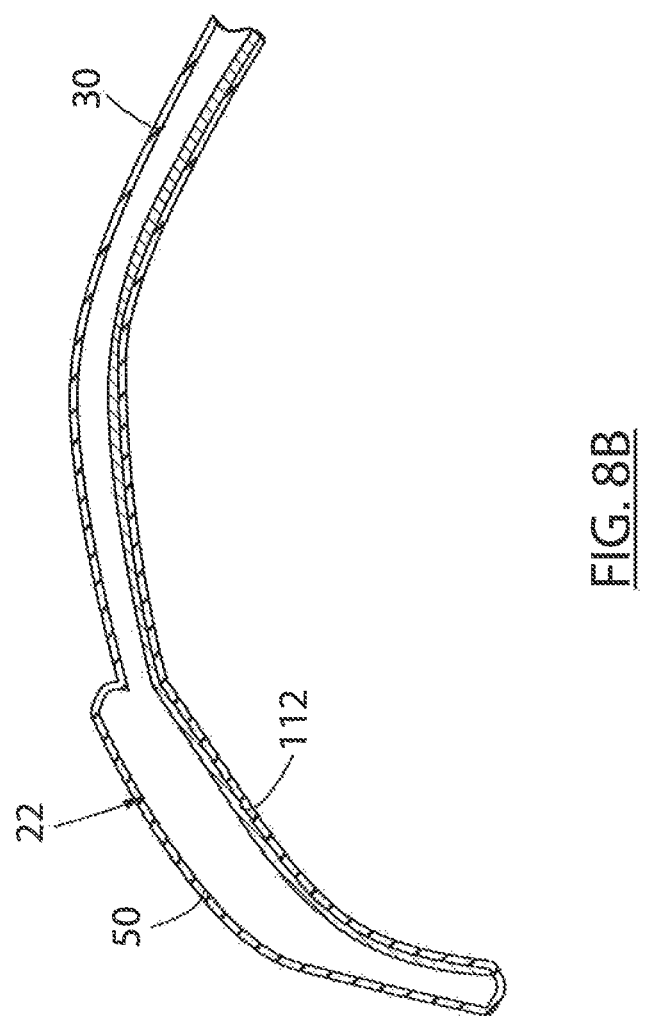

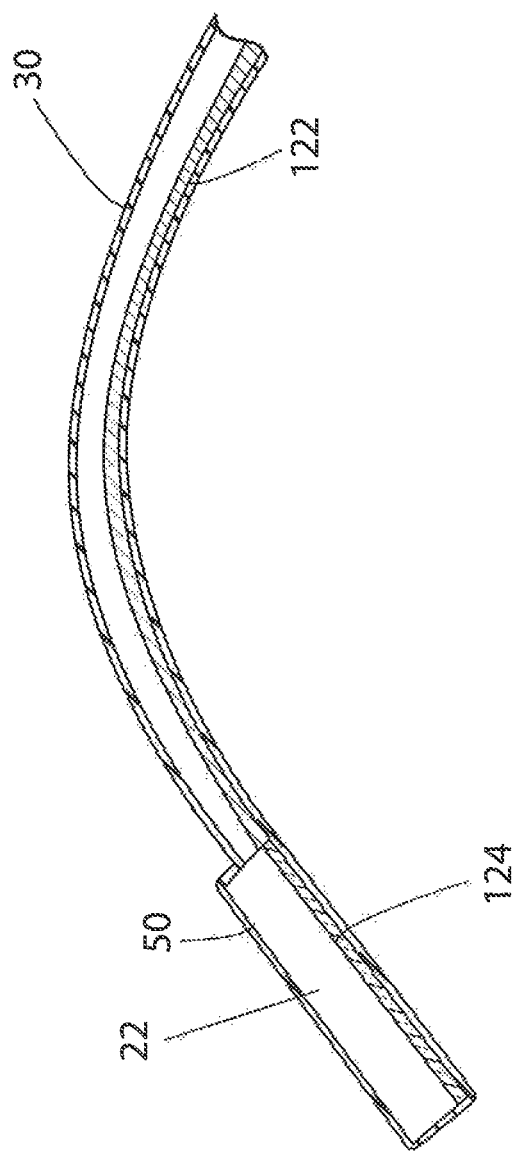

INTRA-ESOPHAGEAL BALLOON SYSTEM

CROSS-REFERENCE TO RELATED APPLICATIONS

This application is a continuation-in-part of U.S. patent application Ser. No. 15/786,707, filed Oct. 18, 2017, and entitled METHOD OF USING AN INTRA-ESOPHAGEAL BALLOON SYSTEM; which is a divisional of U.S. patent application Ser. No. 12/847,018, filed Jul. 30, 2010, and entitled INTRA-ESOPHAGEAL BALLOON SYSTEM; which claims priority from U.S. Provisional Patent Application Ser. No. 61/272,564, filed on Oct. 6, 2009, the entire contents of each of each of which is hereby expressly incorporated by reference into the present application in its entirety.

BACKGROUND OF THE INVENTION

1. Field of the Invention

The invention generally relates to atrial ablation procedures. More particularly, the invention relates to a method and apparatus for moving a patient's esophagus away from an ablation site to prevent accidental damage to the esophagus during the performance of an ablation.

2. Discussion of the Related Art

One method of treating atrial fibrillation has been to perform ablation of selected areas of the left atrium. Typically, ablations of this type are carried out via an intravascular catheter using radiofrequency or microwave energy to cause thermal damage to the selected parts of the left atrial tissue. The posterior wall of the left atrium is particularly targeted for ablation because the pulmonary veins enter the atrium at this area of the left atrium. Thus, encircling the pulmonary veins with continuous rings of lesions is common in this procedure. The esophagus may however, be positioned so as to overlie one or more of these veins, thereby making the desired encirclement difficult or impossible. Further, the esophagus is a mobile structure. Thus, peristaltic movements thereof may cause the esophagus to move and change its position relative to the left atrium.

In addition to the foregoing disadvantages, left atrial ablation of this kind also experiences a great deal of unwanted heat dissipation from the ablation catheter tip. Upon application of the catheter tip to the ablation site, the tissue immediately contiguous to the tip is heated, thereby disrupting cellular function thereof. A sufficient amount of heat must be generated to coagulate and denature the proteins in the myocardial cells. If a heat sink is present in close approximation of the ablation site, generating sufficient heat becomes difficult if not impossible using presently available RF generators. For instance, arteries in close approximation to the ablation site experience rapid blood flow sufficient to conduct heat away from the area rapidly.

Left atrial ablation may also be accomplished by introducing a balloon into the left atrium that can be filled with vaporized nitric oxide, thereby causing ablation by freezing the target tissue. This balloon is generally positioned at the mouth of the pulmonary veins and creates ring cryo-lesions around the vein orifices, thus isolating them from the rest of the left atrium. It may also be positioned to create additional lesions on the roof, the posterior wall, or encircling lesions around the left atrial appendage. It has been shown that cryoablation carries equivalent risk of injury to the esophagus as radiofrequency energy, and a greater risk of phrenic nerve damage.

The inventor of the present application previously developed an intra-esophageal balloon system for selectively moving the esophagus away from an ablation site. That system is disclosed in U.S. Pub. App. No. 2011/0082488 (the '488 publication), which is incorporated herein by reference herein. The system disclosed in the '488 publication is characterized by a balloon that is constructed primarily of a flexible material and that is adapted for insertion into a patient's body through the oral cavity of the patient and into the esophagus. The balloon is provided at the distal end of a tube through which pressurized fluid can flow from an external pressure source to inflate the balloon. The balloon has a stiffening strip that extends axially or longitudinally of the balloon and that is attached to or formed on or in the wall of the balloon. Due to the provision of this stiffening strip, the balloon expands asymmetrically upon inflation to force the esophagus which contains the balloon to also bend and move away from the posterior wall of the atrium. Bending of the esophagus may be directed to also push the phrenic nerve away from the pulmonary veins. The balloon may be inflated by a fluid such as air or another inert gas or, more preferably, by a cooled liquid that permits the balloon to also serve as a heat sink. Protection against damage to the esophagus thus can be accomplished by deflecting the esophagus away from the lesion site, and by creating a heat sink (in this case warmed liquid) infused into the balloon The system disclosed in the '488 publication works very well. However, it has been discovered that more controlled and, in some instances, more pronounced esophageal movement may be desired.

SUMMARY OF THE INVENTION

In accordance with an aspect the present invention, an intra-esophageal device of the general type disclosed in the '488 publication can be improved by providing a deflecting member instead of or in addition to the stiffening strip. The deflecting member may be provided in the tube, the balloon, or both, so as to selectively distort to bend the balloon and/or the tube to move the esophagus away from the ablation site. The deflecting member may comprise at least one of 1) a strip that is made of a shape memory material that is responsive to the receipt of a stimulus to deflect to a predetermined shape, 2) a strip that is made of or that contains a ferrous material and that deflects in response to the presence of a magnetic field, and 3) a selectively tensionable element such as a cable, wire, or string. The deflecting member may be supplemented by a stiffening strip located in the balloon.

In one possible configuration, the deflecting member may be formed from a strip of a shape memory material such as nitinol. Upon application of the appropriate stimulus such as heat, the memory material of the deflecting member assumes its preformed shape, bending the tube and/or the balloon. The shape memory material strip may be confined in the tube or may also extend into the balloon.

Upon application of the appropriate stimulus such as heat, the memory material of the deflecting member assumes its preformed shape, bending the tube and carrying the balloon and esophagus with it. One possible deflected shape of the tube may be in a curve, such as the letter C, when the balloon is viewed from the side or in transverse cross section. The deflecting member may be continuous with a stiffening strip in the balloon, which may or may not also have shape memory. If the stiffening strip in the balloon is continuous with the deflecting member in the tube, and both are made of shape memory material, maximal deflection of the esophagus is possible.

Alternatively, a deflecting member could extend into the balloon, and a stiffening strip can be provided diametrically opposite the deflecting member.

The deflecting member may include a tube having a channel with a tensionable element such as a fine string, cable, or wire attached to the distal end of the tube or even the distal end of the balloon. In this case, deflection of the tube carries the balloon and esophagus with it. The tensionable element may alternatively be attached to the distal end portion of the balloon.

Another deflection method comprises a central compartment in the balloon which contains ferromagnetic material in the form of spheres, powder, or fragments. Application of a magnetic impulse from an electromagnet, possibly positioned posterior to the heart, i.e. under the patient, will pull the balloon and esophagus away from the left atrium. The ferrous object could alternatively comprise a ferrous strip provided on or in the wall of the balloon. This method may be used alone, or in conjunction with one of the other deflection methods described herein. Application of a magnetic field from one side may allow deflection of the balloon and esophagus to that side as well.

BRIEF DESCRIPTION OF THE DRAWINGS

Preferred exemplary embodiments of the invention are illustrated in the accompanying drawings, in which like reference numerals represent like parts throughout, and in which:

FIGS. 2A-2C are somewhat schematic side sectional elevation views of an intra-esophageal balloon system constructed in accordance with a first embodiment of the invention and characterized by a deflecting member located in the balloon and formed from a shape memory material, and showing the balloon in various operational states;

FIGS. 3A-3C are somewhat schematic side sectional elevation views of an intra-esophageal balloon system constructed in accordance with a second embodiment of the invention and characterized by a ferrous strip located in the balloon;

FIGS. 6A and 6C are somewhat schematic side sectional elevation views of an intra-esophageal balloon system constructed in accordance with a firth embodiment of the invention and characterized by a deflecting member extending the entire length of the balloon and the distal end portion of the tube and formed from a tensionable element;

FIGS. 8A and 8B are somewhat schematic side sectional elevation views of an intra-esophageal balloon system constructed in accordance with a seventh embodiment of the invention and characterized by a deflecting member extending the entire length of the balloon and the distal end portion of the tube and formed from a strip of a shape memory material; and FIGS. 9A and 9B are somewhat schematic side sectional elevation views of an intra-esophageal balloon system constructed in accordance with an eighth embodiment of the invention and characterized by a stiffening strip located in the balloon and deflecting member confined to the tube and formed from strip of a shape memory material.

DETAILED DESCRIPTION OF THE PREFERRED EMBODIMENTS

Figure 1A:
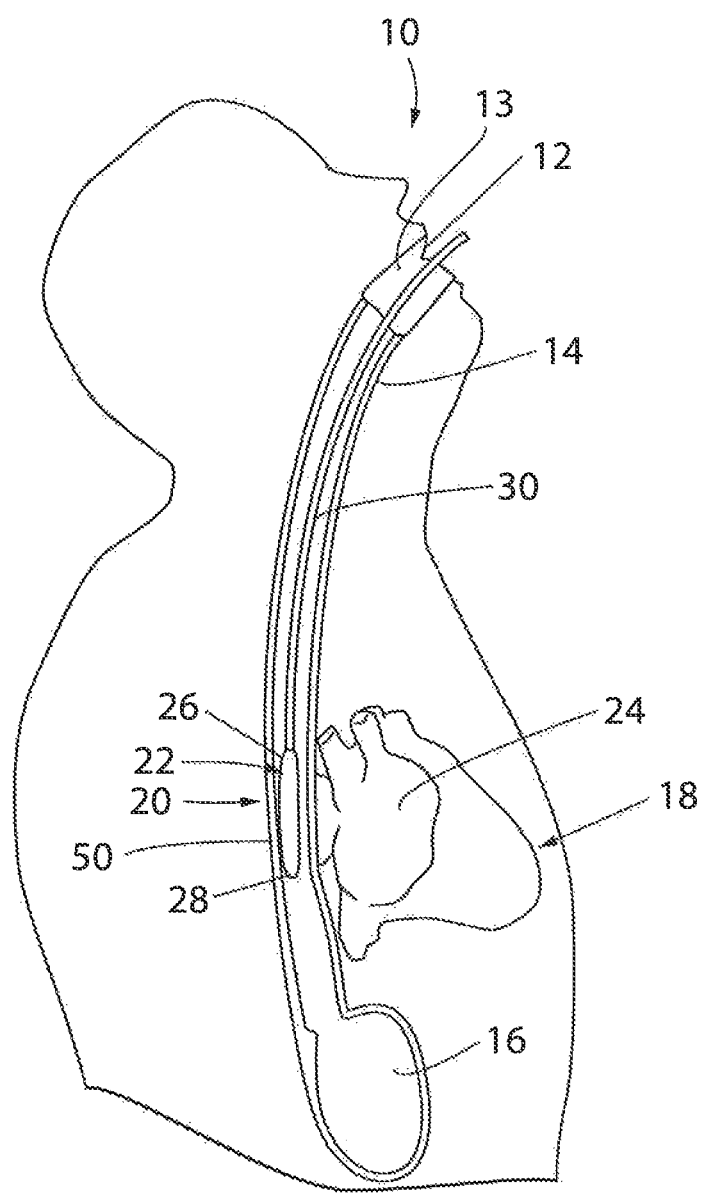
FIGS. 1A-1C are schematic illustrations of a patient having an intra-esophageal balloon system constructed in accordance with a preferred embodiment the invention inserted into the patient's esophagus.

Referring now to the drawings, and initially to FIG. 1A, a schematic illustration of a portion of the internal organs of a patient 10 is provided with an intra-esophageal balloon system 20 constructed in accordance with a preferred embodiment of the invention inserted therein. Patient 10 has a mouth 12 leading to the esophagus 14, which then terminates at an opening of the stomach 16. The esophagus 14 is in close proximity to patient's heart 18, placing the esophagus at risk to injury during left atrial ablation. The intra-esophageal balloon system 20 is inserted through the patient's mouth 12 and oral cavity 13 and into the esophagus 14. In particular, a balloon 22 of the system 20 is positioned within the esophagus 14 at a point substantially lateral to a left atrium 24 of the heart 18. Balloon 22 comprises a proximal or upper end 26 and a distal or lower end 28 opposite proximal end 26. Proximal end 26 is interconnected with a tube 30 that extends upwardly through the esophagus 14 and through patient's mouth 12 to a source of pressurized liquid. The balloon 22 and/or tube 30 are designed to bend, distort, or otherwise move the esophagus 14 away from the heart 18 and facilitate left atrial ablation without thermal injury to the esophagus. Balloon 22 may be configured to be inflated to pressures of approximately 8-10 atmospheres. When balloon 22 is inflated, balloon 22 may be 4-7 cm long and less than or equal to 3.0 cm in diameter, although alternative ranges are envisioned and are within the scope of the present invention. A relief valve (not shown) may if desired be disposed at the distal end 28 of the balloon 22 to prevent its over-inflation. The balloon 22 preferably is inflated with a liquid such as saline, admixed with radiopaque contrast material, although air or another inert gas could be used to inflate balloon 22.

Balloon 22 comprises an elongate, relatively narrow body 50 constructed of silicone, rubber or a similar flexible material that may be safely introduced into the esophagus. Body 50 is generally circular in cross-section when uninflated so as to be symmetrical about a longitudinal bisector, though it is contemplated that the balloon 22 may be more ovoid or have other shapes, so long as the balloon can be inserted into the patient's esophagus 14 in its deflated state and inflated as discussed below.

Figure 1B:
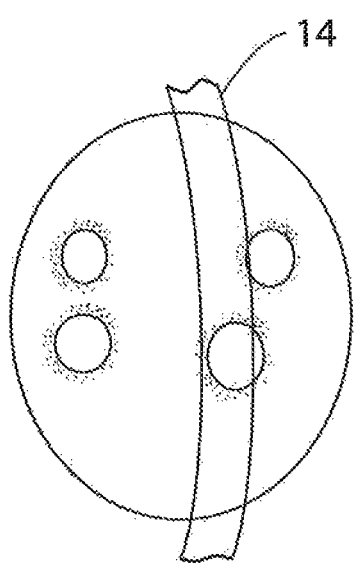
Figure 1C:
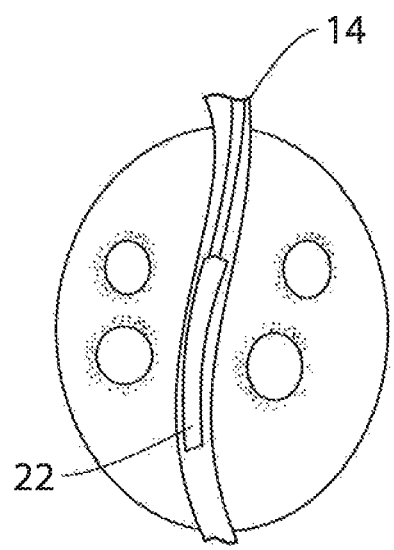

Balloon 22 is configured to distort, move, and/or to expand asymmetrically when inflated so as to distort the esophagus 14 away from the heart 18 using one or more deflecting members and/or one or more stiffening strips as described in more detail below. Asymmetrical expansion may be made possible by rendering the balloon circumferentially non-uniformly flexible. Stated another way, the balloon includes a first portion and a second portion that is more flexible than the first portion. This effect is most easily achieved by making at least one side or edge portion of the balloon more or less flexible than at least one other side or edge portion of the balloon. In use, the esophagus 14 ordinarily overlies the left atrium as shown in FIG. 1B. The location of the pulmonary vein orifices is marked. The esophagus is seen to overlie the orifice of the veins. Cryoablation of these veins would result in damage to the esophagus. Deflection of the balloon 22 and possibly the tube 30 in response to operation of a stiffening strip and/or the deflecting member, however, moves the esophagus 14 away from the orifice of the pulmonary vein as shown in FIG. 1C, avoiding damage from thermal injury.

Figure 2C:
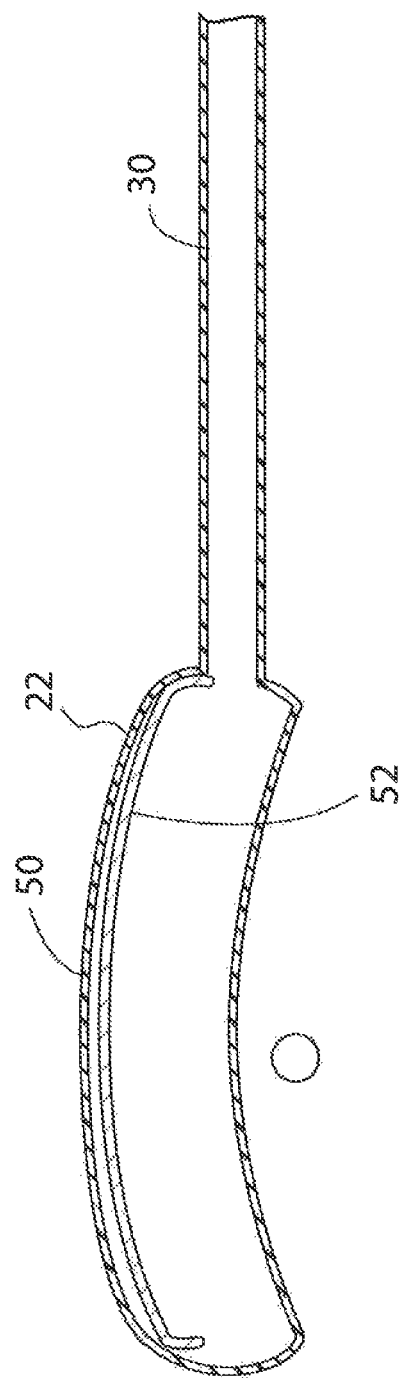
Figure 2D:
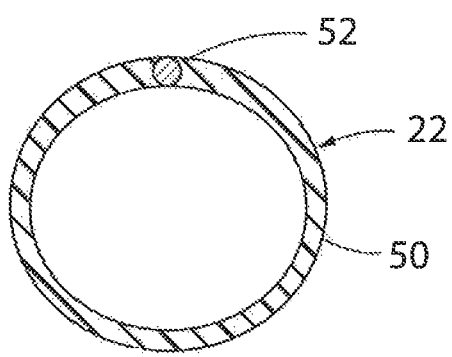
FIG. 2D is a sectional end view of the balloon in the inflated state depicted in FIGS. 2B and 2C.

Referring to FIGS. 2A-2D, a balloon 22 and double-lumen tube 30 are illustrated with a first embodiment of a deflecting member 52. The deflecting member 52 of this embodiment is located inside the body of the balloon 22 and extends longitudinally of the balloon at least substantially the entire length of the body 50. It may be about as wide an average width of a patient's esophagus or approximately 1 mm to 3 cm. It may be anchored to the inner surface of the body 50 by anchors 54 (shown only in FIG. 5C) that allow the deflecting member 52 to slide axially relatively to the body 50 while preventing any significant relative circumferential or radial movement therebetween. Deflecting member 52 is constructed of a shape memory material that may be a metal alloy, such as nitinol, or a shape memory polymer. These materials can be pre-formed into a specific shape. In the case of nitinol, a chromium titanium alloy, application of heat with the material held in its specific shape, followed by quenching, results in the nitinol having a preformed shape. The nitinol strip is shaped in the form of a C during manufacture. After quenching, the deflecting member 52 is straightened out to allow easy introduction into the human esophagus (FIG. 2A). The balloon and esophagus overlie the area of potential thermal injury caused by radiofrequency ablation or "RF ablation" at this time. After deployment in the esophagus at the time of the procedure, the balloon 22 is oriented so that, when the deflecting member 52 achieves its preprogrammed shape, the entire balloon 22 bends or bows so as to be displaced away from the ablation site as shown by the positioning of the balloon 22 in FIGS. 2B and 2C. The resultant displacement of the esophagus can be to one side, or posteriorly away from the esophagus, or both. The deflecting member 52 may be by the side of the balloon 22 closest to the thermal source as shown in FIG. 2B or on the side of the balloon 22 that faces away from the thermal source as seen in FIG. 2C. In either event, the deflecting member 52 deflects the balloon 22 and esophagus away from the thermal source Several methods are available to activate the preprogrammed shape of the deflecting member 52. These methods include the achievement of a specific temperature by the shape memory material, e.g. warming by body temperature or injection of hot water into the balloon; by the passage of an electric current to the strip; by the application of RF or X ray energy to the strip; by activation by a light source introduced into the esophagus; or by the use of a magnetic field. Variations in alloy composition and duration of heating allow the tailoring of the "triggering temperature" in the case of nitinol. While heating the shape memory material may be the most convenient method of triggering, the other methods outlined above may also be used.

Various polymers are also available which have shape memory.

Alternatively, the deflecting member 52 may be a flexible structure that does not expand or increase in length, but that can bend sideways.

Figure 4A:
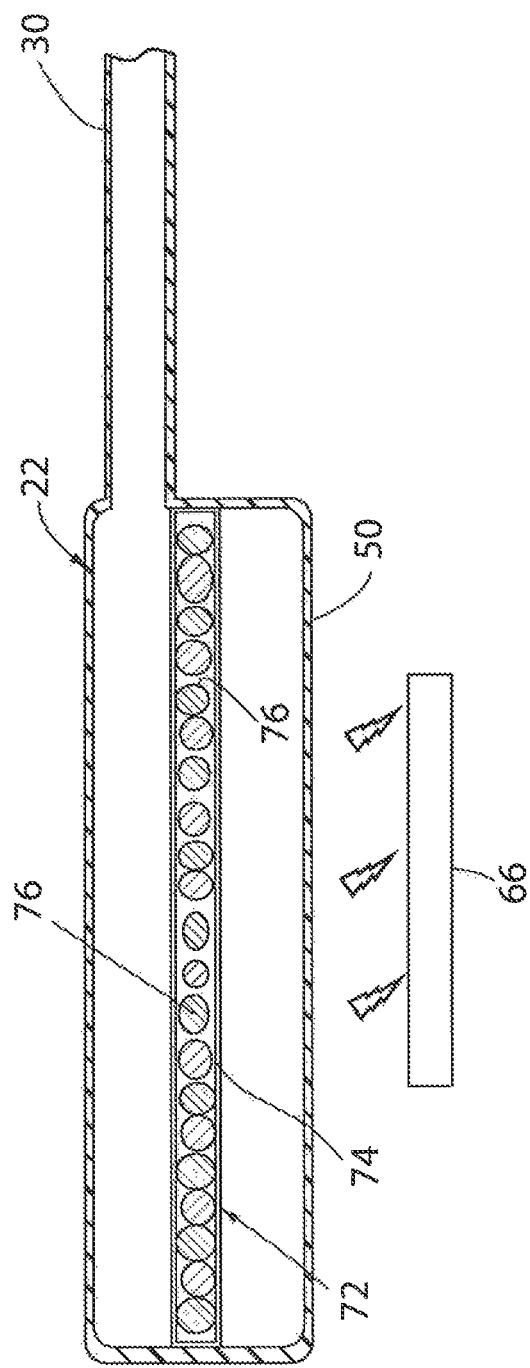
FIGS. 4A, 4B, and 4D are somewhat schematic side sectional elevation views of an intra-esophageal balloon system constructed in accordance with a third embodiment of the invention and characterized by a tube containing ferrous items located in the balloon.
Figure 4B:
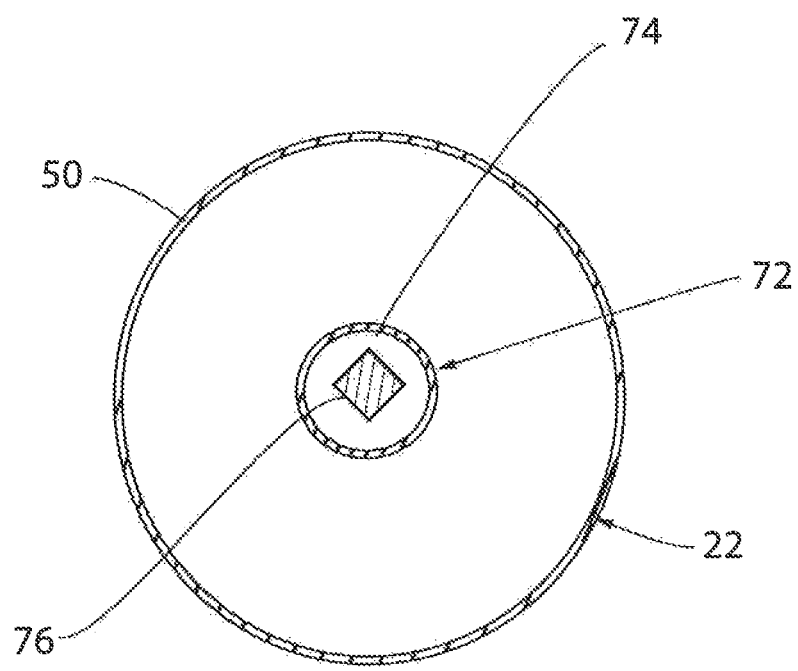
Figure 4C:
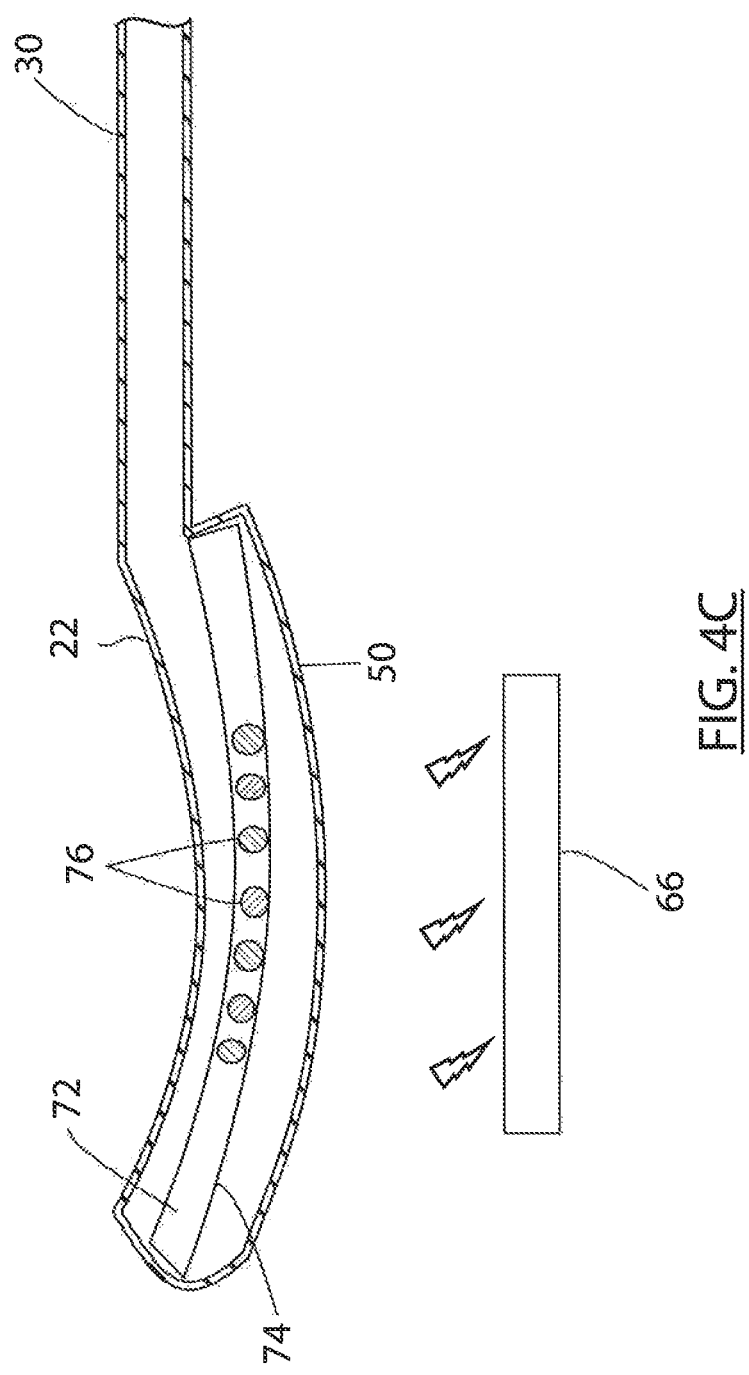
FIG. 4C is a sectional end view of the balloon in the inflated state depicted in FIG. 4B.
Figure 4D:
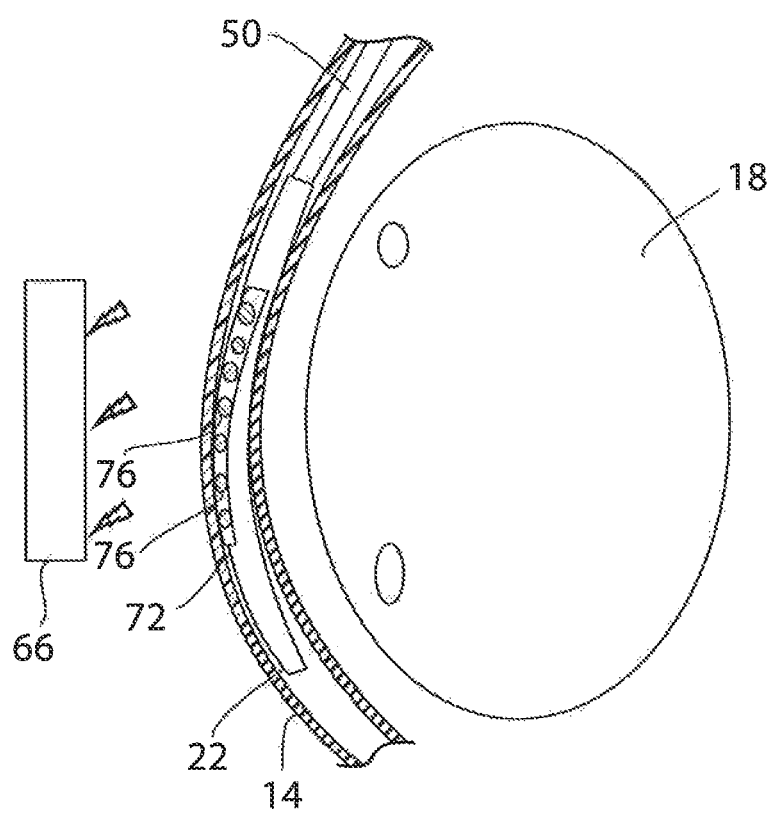

Examples of deflecting members responsive to magnetic fields are illustrated in FIGS. 3A-4C. Referring first to FIG. 3A, the deflecting member 62 could be formed from a ferromagnetic strip mounted on or in the sidewall of the body 50 of the balloon 22. The side of the balloon 22 bearing the strip 62 is positioned in the esophagus adjacent the left atrium in use as seen in FIG. 3B. Strip 62 is responsive to operation of an electromagnet 66 to so that the balloon 22 distorts as whole to move the esophagus away from the left atrium as shown in FIG. 4C. Alternatively, the deflecting member 72 could be formed from a tube 74 containing small ferrous objects 76 such as iron fillings or small ball bearings as shown in FIGS. 4A-4C. The tube 74 could be a central channel in the balloon 22. The side of the balloon 22 bearing the strip 62 or 72 is positioned in the esophagus adjacent the left atrium in use. Deflecting member 62 or 72 may be responsive to operation of an electromagnet 66 to cause the balloon 22 to distort to move the esophagus away from the left atrium. The magnet 66 may be positioned beneath a supine patient as shown in FIG. 4C, or it may be positioned to the posterior to the esophagus as shown in FIG. 4D. In both cases, the balloon 22 may be filled with warm water prior to cryoablation so that the balloon 22 acts as a heat sink. The amount of deflecting member and esophagus movement can be controlled by controlling the strength of the magnetic field generated by magnet 66 and/or the distance between the magnet 66 and the deflecting member 62 or 72.

In all cases described above, the deflecting member could be provided in at least the distal end portion of the tube 30 instead of or in addition to being provided in the balloon 22.

It is also possible to provide a stiffening strip on or in the balloon, either alone or in combination with a deflecting member. The stiffening strip causes asymmetrical expansion of the balloon by rendering the balloon circumferentially non-uniformly flexible. The stiffening strip, if present, preferably is applied along one relatively peripheral narrow portion of balloon at a location at or near the portion of the esophagus 14 that is closest to the patient's heart 18 and extends lengthwise from proximal end 26 to distal end 28 without extending distally beyond the distal end. Stiffening strip preferably has a width similar to that of an average width of a patient's esophagus for reasons that will be made apparent from the ensuing description. In particular, stiffening strip may have a width of approximately 1 mm to 2 cm. In particular, stiffening strip is configured to inhibit or prevent a portion of balloon 22 from expanding during inflation of balloon 22.

Figure 5A:
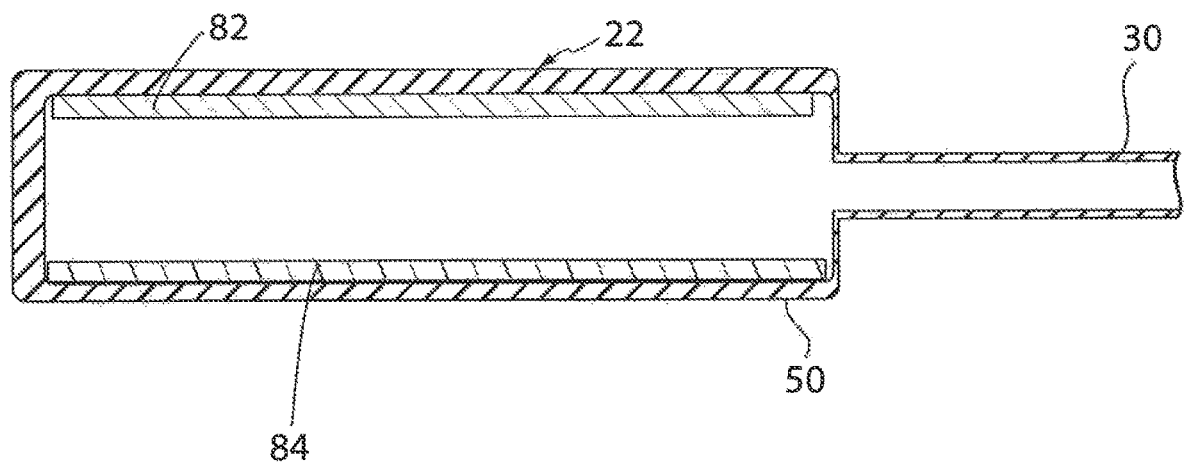
FIGS. 5A and 5C are somewhat schematic sectional elevation various views of an intra-esophageal balloon system constructed in accordance with a fourth embodiment of the invention and characterized by a deflecting member located in the balloon and a stiffening strip located in an opposite side of the balloon.
Figure 5B:
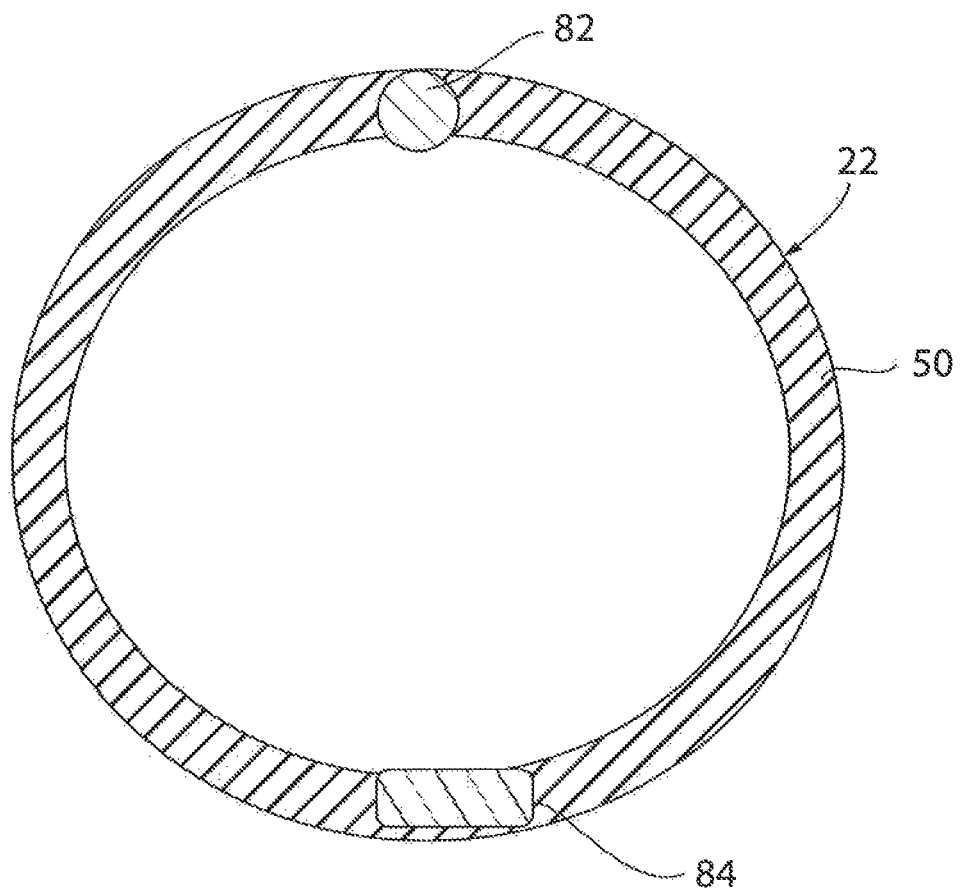
FIG. 5B is a sectional end view of the balloon in the inflated state depicted in FIGS. 5A and 5C.
Figure 5C:
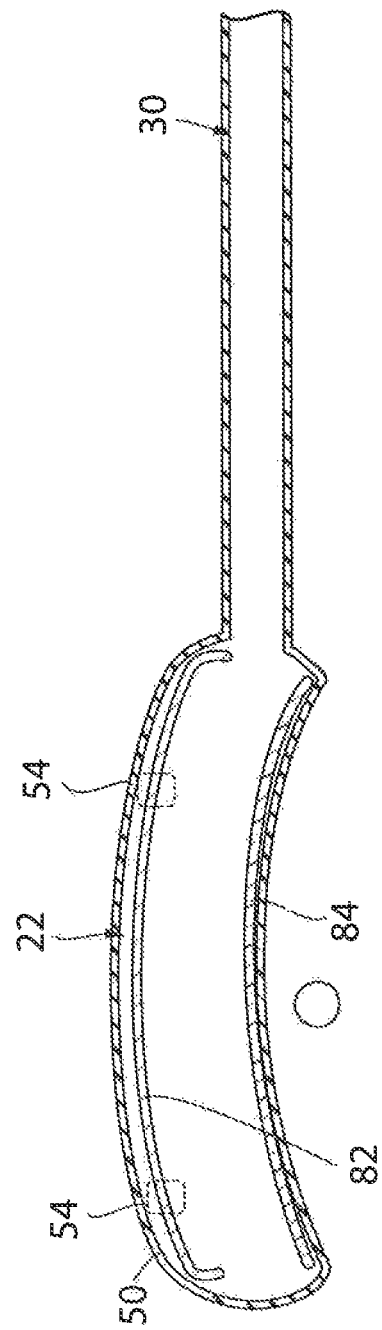

Referring to FIGS. 5A-5C a stiffening strip 84 is shown in combination with a deflecting member 82, with the elements 82 and 84 being located on opposite sides of the balloon 22. More specifically, the deflecting member 82 is formed from a nitinol strip or a strip of another material having a shape memory. This deflecting member could be provided on or in the sidewall of the body 50 of the balloon 22 and could extend longitudinally along at least the entire length of the balloon 22. A longitudinally-extending stiffening strip 84 is provided on or in the sidewall of the body 50 diametrically opposite the deflecting member 82. The stiffening strip 44 could be formed, for example, from a piece of relatively rigid plastic or a metal wire. It also could be formed from a shape memory material. In this case, inflation of the balloon 22 causes the balloon 22 to deflect away from the ablation site as shown in FIG. 5C, and activation of the shape memory material of deflecting member 82 aides in this deflection.

Figure 6A:
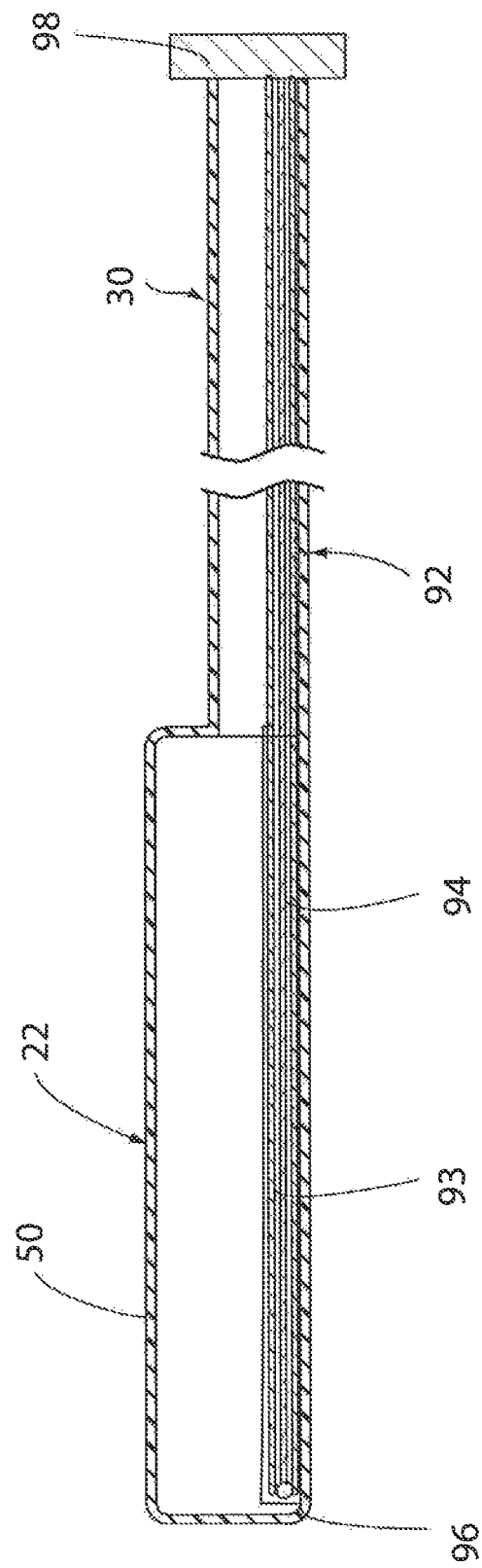
Figure 6B:
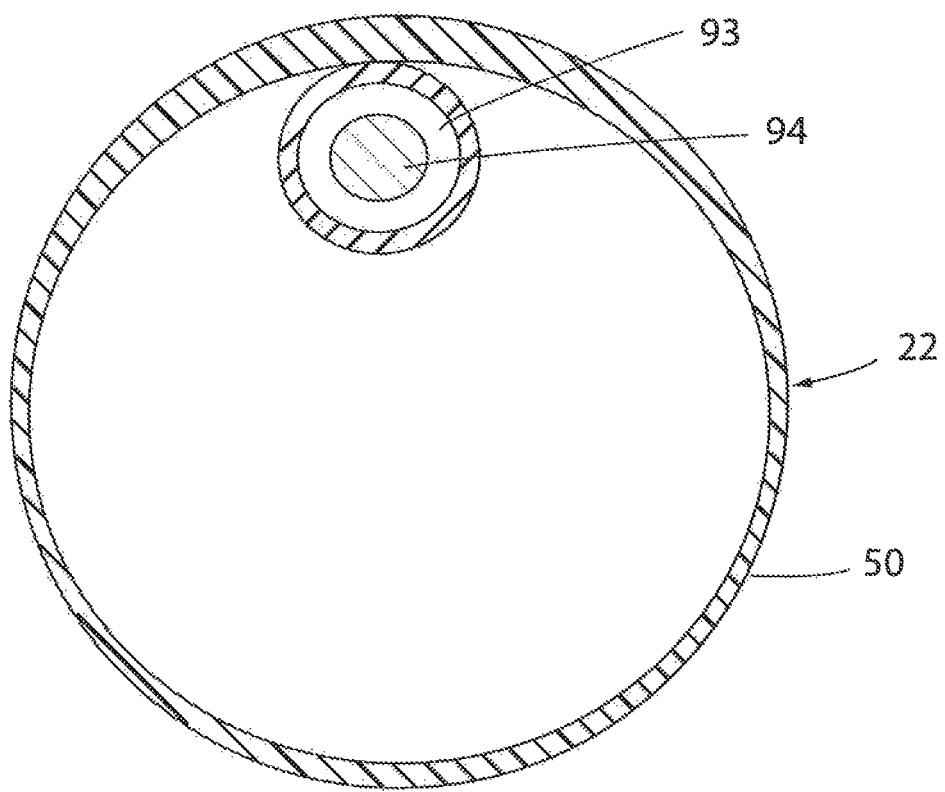
FIG. 6B is a sectional end view of the balloon depicted in FIG. 6A.
Figure 7A:
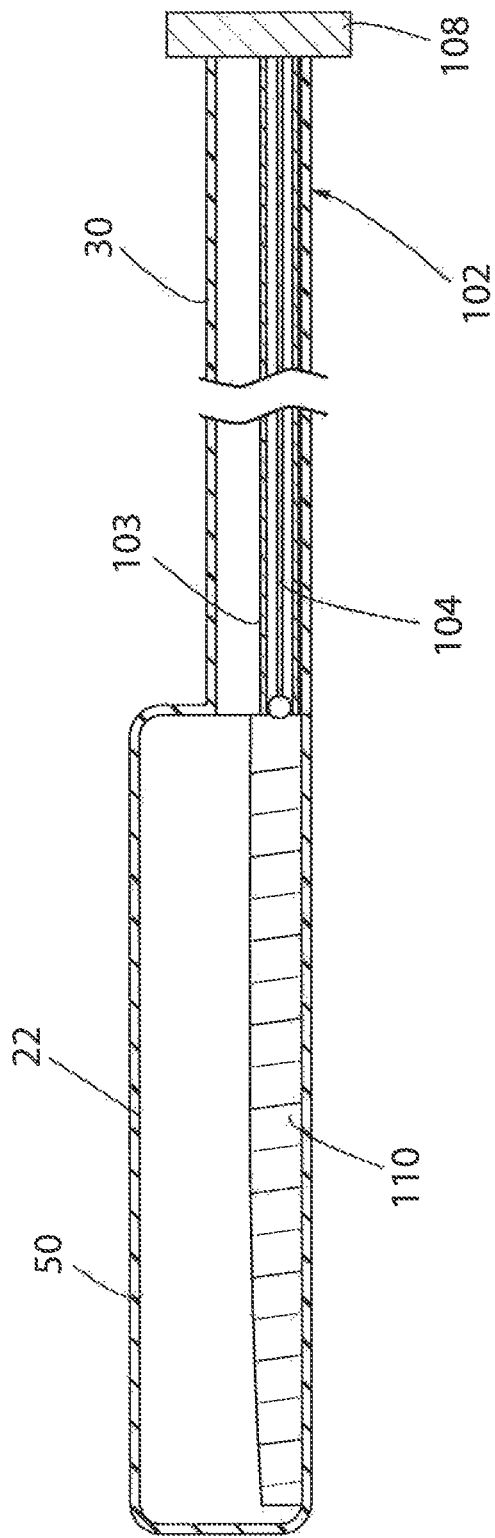
FIGS. 7A and 7B are somewhat schematic side sectional elevation views of an intra-esophageal balloon system constructed in accordance with a sixth embodiment of the invention and characterized by a stiffening strip located in the balloon and a deflecting member confined to the tube and formed from a tensionable element.
Figure 7B:
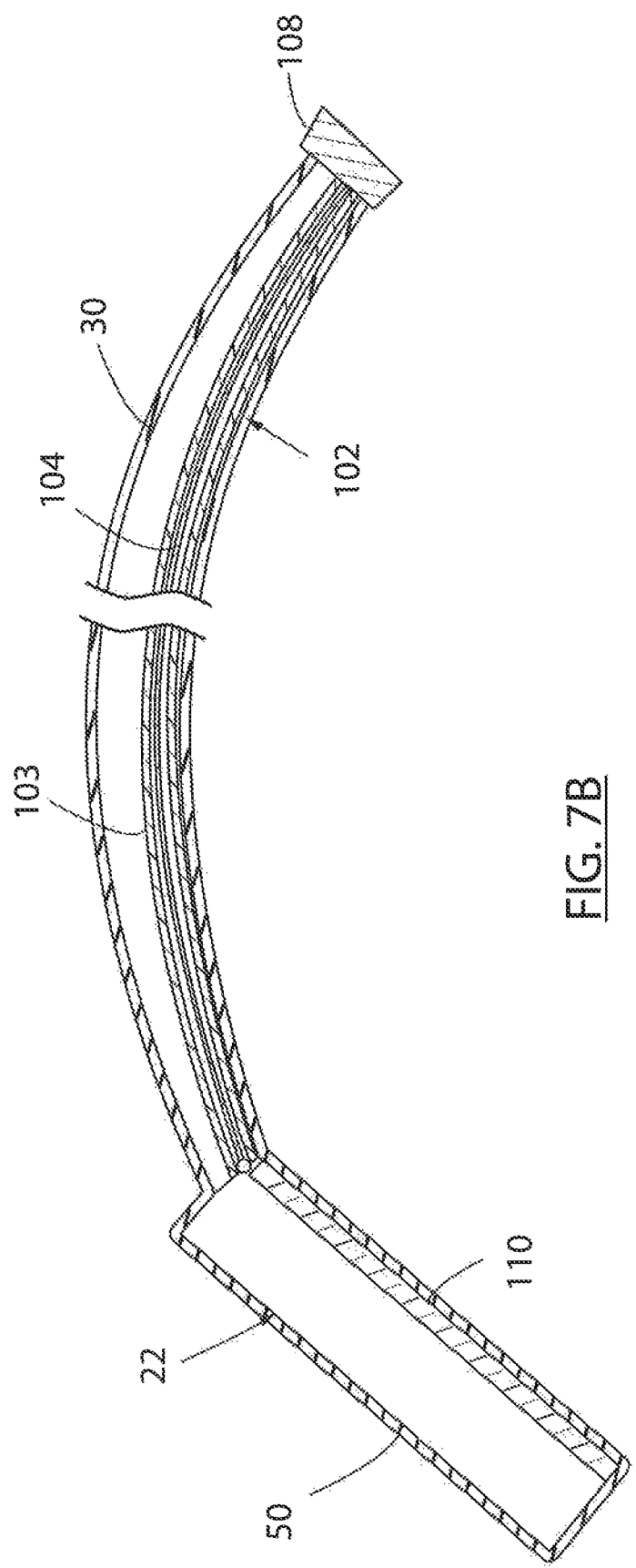

Referring to FIGS. 6A-6C, the deflecting member 92 may include a longitudinally-extending channel 93 in the double-lumen tube 30 and the body 50 of the balloon 22 for receiving a tensionable element 94, such as a fine cable, wire. The tensionable element 94 has a proximal end extending beyond proximal end of the tube 30 and a distal end affixed to the distal end of the balloon 22. The portion of the deflecting member 92 that is located within the balloon 22 may be imbedded in a strip 96 that is stiffer than the remainder of the balloon 22 but that is flexible enough to bend or distort with the deflecting member 92. In use, retraction of the tensionable element 94 pulls the distal end of the balloon 22 toward the proximal end to cause deflection of the balloon 22. Retraction may be accomplished by a screw mechanism 98 or similar mechanism in a handle 100 located at or beyond the proximal end of the tube 30. In a variant, shown in FIGS. 7A and 7B, the channel 103 of the deflecting member 102 extends only the length of the tube 30, with the inner end of the tensionable element 104 being anchored to the proximal end of the balloon 22. A longitudinally-extending stiffening strip 110 is located in or on the balloon 22 in alignment with the channel 103. With this arrangement, inflation of the balloon 22 leads to asymmetric expansion as discussed above, and additional balloon and tube motion movement are achieved by manipulation of a screw mechanism 108 to pull the distal end of the tube 30 toward the proximal end as shown in FIG. 7B.

Other combinations also could be used to deflect both the balloon 22 and the tube 30.

For example, as shown in FIGS. 8A and 8A, a deflecting member 112 formed from a strip of nitinol or other material having a memory shape could extend the entire longitudinal length of the balloon 22 and through at least the distal end portion of the double-lumen tube 30. The deflecting member 112 could be mounted on or imbedded in the wall of the balloon body 50 and/or the tube 30.

Figure 9A:
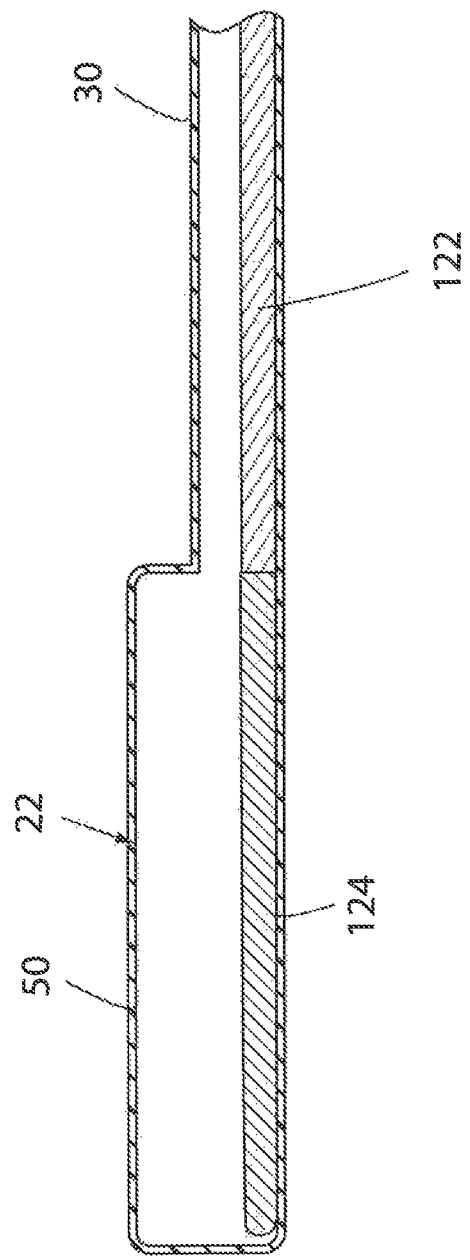

Alternatively, referring to FIGS. 9A and 9B, the nitinol or other memory material forming the deflecting member 122 could extend only the length of the tube 30 or at least the distal portion thereof, and a stiffening strip 124 could be located in or on the balloon 22 in alignment with the deflecting member 122. With this arrangement, inflation of the balloon 22 leads to asymmetric expansion due to the presence of stiffening strip 124, and additional balloon and tube motion are achieved by distortion of the shape memory material forming the deflecting member 122 upon the receipt of an appropriate stimulus such as temperature change, magnetic attraction, UV exposure, etc.

The devices described herein, and other devices falling within the scope of the present invention, can also protect the esophagus against injury during cryoablation. In cryoablation, specific portions of the left atrium are cooled to subzero temperatures, usually by the application of an occluding balloon to the orifices of the pulmonary veins. The occluding balloon is then filled with vaporized nitrous oxide, thereby creating a ring of cryo-damaged atrial tissue surrounding each pulmonary vein. The damaged tissue does not conduct electrical impulses, and it serves to "isolate" the pulmonary veins from the rest of the atrium.

It has been shown that cryoablation is also associated with the same risk of esophageal damage seen with RF ablation, when the esophagus is contiguous to the pulmonary veins.

To prevent cryo-damage to the esophagus, two strategies are available with the esophageal balloon:
 a) Preheating the esophagus with warmed saline for several minutes prior to application of cryoenergy and retaining warmed fluid during cryoablation.
 b) Deflection of the esophagus away from the cryo-site using any or all of the methods used for deflection during RF ablation.

Pre-warming and warming of the esophagus is unlikely to provide the same degree of protection as cooling the esophagus during RR The esophagus may be safely heated to about 110° F., i.e. 12° F. higher then body temperature. It can be safely cooled to 5° F., a 93° F. differential. It has been shown in animal studies and in vitro that pre-cooling the esophagus with a balloon using saline at 5° C. prevents thermal damage to the esophagus during RF of the atrial tissue. The same has not been shown with pre-warming or warming of the esophagus, but it may be an alternative method of protection.

Deflection of the esophagus becomes more important here, along with some protection conferred by gentle heating. Heat sensitive shape memory materials are likely to be the best option. The introduction of warm water at, for example, 110° F. to activate the shape memory gives a wider range over ambient body temperature, allowing for easier design of the shape memory material and avoiding inadvertent activation of the material by manual handling or during transportation. (FIGS. 6A and 6B.)

Although the best mode contemplated by the inventors of carrying out the present invention is disclosed above, practice of the present invention is not limited thereto. It will be manifest that various additions, modifications and rearrangements of the aspects and features of the present invention may be made in addition to those described above without deviating from the spirit and scope of the underlying inventive concept. The scope of some of these changes is discussed above. The scope of other changes to the described embodiments that fall within the present invention but that are not specifically discussed above will become apparent from the appended claims and other attachments.

What is claimed is:

1. A method of moving a human esophagus, comprising the steps of:
 inserting an uninflated selectively inflatable balloon into a patient's esophagus, the balloon being coupled to a distal end of a tube;
 inflating the balloon;
 deflecting a deflecting member located at least in part in the balloon, thereby deflecting at least the balloon to cause the balloon to bend or bow so as to move at least a portion of the esophagus away from an initial position thereof;
 ablating tissue of the patient's heart; then
 deflating the balloon and returning the deflecting member to its original shape; and then
 removing the balloon from the esophagus.

2. The method of claim 1, wherein, when the balloon is inserted into the esophagus, a first portion of the balloon is positioned closer to the patient's heart than a second portion, wherein the second portion is more flexible than the first portion, and wherein the at least a portion of the esophagus moves away from the patient's heart as a result of balloon inflation.

3. The method of claim 2, wherein the first portion comprises a strip of material that extends longitudinally of the balloon and that is located on or in a sidewall of the balloon.

4. The method of claim 1, wherein the step of inflating the balloon is accomplished by pumping a pressurized liquid into the balloon.

5. The method of claim 4, wherein the step of inflating is performed with a cold or warmed liquid that serves to provide the esophagus with a heat sink such that the esophagus is further protected against injury during the ablating step.

6. The method of claim 1, wherein, at a maximum point of distortion thereof, the esophagus moves at least 5 mm laterally away from its initial position as a result of balloon inflation.

7. The method of claim 6, wherein, at the maximum point of distortion thereof, the esophagus moves at least 20 mm laterally away from its initial position as a result of balloon inflation.

8. The method of claim 1, wherein the deflecting member comprises at least one of:
   (A) a strip made of a shape memory material that is responsive to the receipt of a stimulus to deflect to a predetermined shape,
   (B) a strip that is made of or contains a ferrous material and that deflects in response to the presence of a magnetic field, and
   (C) a selectively tensionable cable, wire, or string.

9. The method of claim 1, wherein the deflecting member comprises a strip that is made of a shape memory material, and further comprising applying a stimulus to the shape memory material to deflect the deflecting member to a predetermined shape.

10. The method of claim 9, wherein the deflecting member extends along at least one of 1) at least a distal end portion of the tube, and 2) at least a majority of a longitudinal extent of the balloon.

11. The method of claim 9, further comprising a stiffening strip that is located in the balloon and that extends longitudinally of the balloon, wherein the stiffening strip distorts less than the surrounding portions of the balloon during balloon inflation so that the balloon as a whole expands asymmetrically about a longitudinal centerline thereof to deflect the esophagus away from the ablation site.

12. The device of claim 11, wherein the stiffening strip is positioned on a common side of the balloon as the deflecting member and is in alignment with the deflecting member.

13. The method of claim 11, wherein the stiffening strip is located at least generally diametrically opposite the deflecting member.

14. The method of claim 1, wherein, when inflated, the balloon is 4-7 cm long.

15. The method of claim 1, wherein, when inflated, the balloon has a maximum diameter of less than 3.0 cm.

16. A method of moving a human esophagus, comprising the steps of:
   inserting an uninflated selectively inflatable balloon into a patient's esophagus, the balloon being coupled to a distal end of a tube;
   inflating the balloon;
   using a deflecting member located in at least one of the tube and the balloon, deflecting at least one of the balloon and the tube to cause the balloon to move at least a portion of the esophagus away from an initial position thereof;
   ablating tissue of the patient's heart; then
deflating the balloon and returning the deflecting member to its original shape; and then removing the balloon from the esophagus, wherein
   the deflecting member comprises a strip that is made of a shape memory material, and further comprising applying a stimulus to the shape memory material to deflect the deflecting member to a predetermined shape, and wherein
   applying a stimulus comprises heating or cooling the deflecting member.

17. A method of moving a human esophagus, comprising the steps of:
   inserting an uninflated selectively inflatable balloon into a patient's esophagus, the balloon being coupled to a distal end of a tube;
   inflating the balloon;
   heating or cooling a shape-memory deflecting member located in at least one of the tube and the balloon to cause the deflecting member to deflect at least one of the balloon and the tube to cause the balloon to move at least a portion of the esophagus away from an initial position thereof relatively proximal the patient's heart to a deflected position relatively remote from the patient's heart;
   ablating tissue of the patient's heart; then
   deflating the balloon and returning the deflecting member to its original shape; and then
   removing the balloon from the esophagus.

* * * * *